US010023708B2

(12) United States Patent
Alm et al.

(10) Patent No.: US 10,023,708 B2
(45) Date of Patent: Jul. 17, 2018

(54) METHOD OF PRODUCING A DELIVERY DEVICE

(71) Applicant: PTT HOLDING APS, Lyngby (DK)

(72) Inventors: Martin Alm, Greve (DK); Søren Langer Steffensen, København NV (DK)

(73) Assignee: PTT HOLDING APS, Lyngby (DK)

( * ) Notice: Subject to any disclaimer, the term of this patent is extended or adjusted under 35 U.S.C. 154(b) by 1011 days.

(21) Appl. No.: 14/360,423

(22) PCT Filed: Nov. 23, 2012

(86) PCT No.: PCT/DK2012/050431
§ 371 (c)(1),
(2) Date: May 23, 2014

(87) PCT Pub. No.: WO2013/075724
PCT Pub. Date: May 30, 2013

(65) Prior Publication Data
US 2014/0303263 A1    Oct. 9, 2014

(30) Foreign Application Priority Data
Nov. 23, 2011   (DK) .................................. 2011 00919

(51) Int. Cl.
| C08J 7/02 | (2006.01) |
| A61K 47/32 | (2006.01) |
| A61K 47/34 | (2017.01) |
| A61K 31/415 | (2006.01) |
| A61K 45/06 | (2006.01) |
| A61K 9/00 | (2006.01) |
| A61K 9/70 | (2006.01) |
| A61L 27/18 | (2006.01) |
| A61L 27/54 | (2006.01) |
| A61L 29/06 | (2006.01) |
| A61L 29/16 | (2006.01) |

(52) U.S. Cl.
CPC ............. *C08J 7/02* (2013.01); *A61K 9/0014* (2013.01); *A61K 9/0051* (2013.01); *A61K 9/70* (2013.01); *A61K 9/7007* (2013.01); *A61K 31/415* (2013.01); *A61K 45/06* (2013.01); *A61K 47/32* (2013.01); *A61K 47/34* (2013.01); *A61L 27/18* (2013.01); *A61L 27/54* (2013.01); *A61L 29/06* (2013.01); *A61L 29/16* (2013.01); *C08J 2300/208* (2013.01); *C08J 2383/04* (2013.01); *C08J 2433/14* (2013.01)

(58) Field of Classification Search
CPC ........................................................ C08J 7/02
See application file for complete search history.

(56) References Cited

U.S. PATENT DOCUMENTS

| 7,687,585 | B2 | 3/2010 | Karthauser | |
| 8,802,197 | B2 * | 8/2014 | Alm | ........................... C08J 7/16 |
| | | | | 427/307 |
| 2002/0052448 | A1 | 5/2002 | Wang et al. | |
| 2006/0148985 | A1 * | 7/2006 | Karthauser | ........... C08F 283/12 |
| | | | | 525/100 |
| 2010/0040870 | A1 * | 2/2010 | Alm | .......................... C08J 7/16 |
| | | | | 428/334 |

FOREIGN PATENT DOCUMENTS

| EP | 0 347 145 A2 | 12/1989 | |
| EP | 0 401 713 A2 | 12/1990 | |
| EP | 0 405 284 A2 | 1/1991 | |
| WO | 03/045448 A1 | 6/2003 | |
| WO | 2005/003237 A1 | 1/2005 | |
| WO | 2005/055972 A2 | 6/2005 | |
| WO | WO 2005055972 A2 * | 6/2005 | ........... A61K 9/0024 |
| WO | 2006/045320 A2 | 5/2006 | |
| WO | 2008/052568 A1 | 5/2008 | |
| WO | 2011/109174 A1 | 9/2011 | |

OTHER PUBLICATIONS

Carelli et al. International Journal of Pharmaceutics 1989, 55, 199-207.*
V. Carelli et al., "Evaluation of the Solution Impregnation Method for Loading Drugs Into Suspension-Type Polymer Matrices: A Study of Factors Determining the Patterns of Solid Drug Distribution in Matrix and Drug Release from Matrix", International Journal of Pharmaceutics, Elsevier BV, NL, Oct. 15, 1989, vol. 55, No. 2-3, pp. 199-207, XP025829128.
The extended European Search Report dated Apr. 15, 2015, by the European Patent Office in corresponding European Application No. 12851092.2. (7 pages).

(Continued)

*Primary Examiner* — Matthew P Coughlin
(74) *Attorney, Agent, or Firm* — Buchanan Ingersoll & Rooney P.C.

(57) ABSTRACT

A method of producing a delivery device for delivering a chemical compound includes i) providing an interpenetrating polymer substrate (IP substrate) having a first continuous polymer comprising rubber and a second polymer having hydrogel or a hydrogelable precursor, where the second polymer is interpenetrating in the first polymer; ii) providing the chemical compound and a loading solvent for the chemical compound; and iii) loading the IP substrate with the chemical compound by subjecting the IP substrate to the loading solvent having the chemical compound under conditions where the loading solvent at least partially swells the second polymer. The chemical compound, the second polymer and the loading solvent are selected such that the work of adhesion ($W_{hc}$) between the second polymer and the chemical compound during at least a part of the loading is at least about 0 J/m².

30 Claims, No Drawings

(56) References Cited

OTHER PUBLICATIONS

Dos Santos et al., "Poly(hydroxyethyl methacrylate-co-methacrylated-beta-cyclodextrin) hydrogels: synthesis, cytocompatibility, mechanical properties and drug loading/release properties", Acta Biomaterialia, (2008), vol. 4, issue 3, pp. 745-755.
Ferreira et al., "Evaluation of poly(2-hydroxyethyl methacrylate) gels as drug delivery systems at different pH values", International Journal of Pharmaceutics, (2000), vol. 194, Issue 2, pp. 169-180.
Garcia et al., "5-Fluorouracil trapping in poly(2-hydroxyethyl methacrylate-co-acrylamide) hydrogels: in vitro drug delivery studies", European Polymer Journal, (2000), vol. 36, Issue 1, pp. 111-122.
Karlgard et al., "In vitro uptake and release studies of ocular pharmaceutical agents by silicon-containing and p-HEMA hydrogel contact lens materials", International Journal of Pharmaceutics, (2003), vol. 257, Issue 1-2, pp. 141-151.
Shaw, "Introduction to Colloid and Surface Chemistry", Third Edition, pp. 68-69.
International Search Report (Form PCT/ISA/210) and the Written Opinion of the International Searching Authority (Form PCT/ISA/237) dated Feb. 18, 2013, by the Nordic Patent Institute in corresponding International Application No. PCT/DK2012/050431. (10 pages).

* cited by examiner

METHOD OF PRODUCING A DELIVERY DEVICE

TECHNICAL FIELD

The invention concerns a method of producing a delivery device for delivering a chemical compound such as a drug, in particular a delivery device for slow and/or controlled release of drug(s) or other chemical compound(s).

BACKGROUND ART

A plurality of methods for delivering chemical compounds is known in the art. In recent years large effort has been applied in developing delivery devices in the form of a polymer matrix, in particular hydrogels, with the chemical compound for release embedded in the matrix.

A study by García et al "5-Fluorouracil trapping in poly(2-hydroxyethyl methacrylate-co-acrylamide) hydrogels; in vitro drug delivery studies", European Polymer Journal 36 (2000) 111-122, describes such delivery devices based on hydrogels where the 5-Fluorouracil was trapped in the gel during its polymerization.

In Ferreira et al. "Evaluation of poly(2-hydroxyethyl methacrylate) gels as drug delivery systems at different pH values", International Journal of Pharmaceuticals 194 (2000)169-180, the influence of the pH value during loading of Salicylic acid in PHEMA gel was tested. The loading was performed by immersing in a liquid comprising the salicylic acid at various pH values.

Karlgard et al. "In vitro uptake and release studies of ocular pharmaceutical agents by silicon-containing and p-HEMA hydrogel contact lens materials", International Journal of Pharmaceuticals 257 (2003)141-151 discloses a study of the uptake and release of different chemical compounds in different types of contact lens. The loading was performed by soaking in a liquid containing the chemical compound. It was found that both the uptake and the release were relatively rapid.

Santos et al. "Poly(hydroxyethyl methacrylate-co-methacrylated-β-cyclodextrin) hydrogels: Synthesis, cytocompatability, mechanical properties and drug loading/release properties" ScienceDirect, Acta Biomaterialia 4 (2008) 745-755, describes loading/release properties of hydrocortisone and acetazolamide in the hydrogel. The loading was performed by immersing in liquid containing the drug. It was found that a slow drug release could be obtained.

WO 2005/055972 discloses a drug delivery device comprising a polymeric matrix and a drug distributed within the matrix. The device is essentially free of solvents in particular organic solvents for the drug. The matrix may be an interpenetrating polymer network (IPN) of a large number of different polymer materials.

The drug delivery device is produced by loading the matrix with a drug using a drug carrier in the form of a gas, a supercritical fluid, a high pressure liquid, or a dense gas-like fluid. A preferred drug carrier includes $CO_2$ in a liquid and/or supercritical state. No specific methods are described.

The object of the invention is to provide a novel method of producing a delivery device for delivering a chemical compound, such as a drug where the method provides a high control of the resulting delivery/release profile of the chemical compound from the drug delivery device and where a long delivery time for delivering the chemical compound from the drug delivery device can be obtained.

DISCLOSURE OF INVENTION

This object has been solved by the present invention as defined in the claims. The method of the invention and embodiments thereof as well as the delivery device of the invention and embodiments thereof have shown to have a large number of advantages which will be clear from the following description. The method of the invention comprises the following:

i) providing an interpenetrating polymer substrate (IP substrate) comprising a first continuous polymer comprising rubber and a second polymer comprising hydrogel or a hydrogelable precursor, where the second polymer is interpenetrating in the first polymer;

ii) providing the chemical compound and a loading solvent for the chemical compound;

iii) loading the IP substrate with the chemical compound by subjecting the IP substrate to the loading solvent comprising the chemical compound under conditions where the loading solvent at least partially swells the second polymer.

The chemical compound, the second polymer and the loading solvent are selected such that the work of adhesion ($W_{hc}$) between the second polymer and the chemical compound during at least a part of the loading is at least about 0 J/m$^2$, preferably $W_{hc} \geq$ J/m$^2$, such as $W_{hc} \geq 10$ J/m$^2$, such as $W_{hc} \geq 15$ J/m$^2$, such as $W_{hc} \geq 20$ J/m$^2$, such as $W_{hc} \geq 30$ J/m$^2$, such as $W_{hc} \geq 35$ J/m$^2$.

The "work of adhesion" between two dissimilar materials is a measure of the energy required to separate the two dissimilar materials from each other. The work of adhesion is indicated with $W_{xy}$, wherein x and y respectively are the two dissimilar materials in question. $W_{xy}$ is herein determined in joule per square meter of contact area of the x and y material to be separated (J/m$^2$). The contact area of the second polymer and the chemical component is proportional to the amount of a given chemical component and accordingly the $W_{hc}$ value could also be determined as J/mol chemical component.

The "work of adhesion" between two dissimilar materials depends normally on the temperature, whereas the pressure practically has no importance, because the delivery device is a solid/liquid system which is essentially incompressible unlike gas and gaseous systems.

Work of adhesion ($W_{hc}$) between the second polymer (h) and the chemical component (c) is determined according to the formula:

$W_{hc} = \gamma_{hn} + \gamma_{cn} - \gamma_{ch}$, wherein $\gamma_{hn}$ is the interfacial tension between h and n, $\gamma_{cn}$ is the interfacial tension between c and n, and $\gamma_{ch}$ is the interfacial tension between c and h, where h=second polymer, n=normal saline and c=chemical component.

The respective values of interfacial tension can be determined by any well known method or they can be calculated. Interfacial tensions can be determined from surface tensions of the individual compound, which can be measured or estimated from e.g. HSP which can be measured or estimated from group contribution calculations based on the chemical structure of the individual compound in question.

There are several methods in the art useful for measuring surface tension. The most common is a technique developed by P. Lecomite duNouy. The technique has become known as the duNouy Ring Method. There are many commercial tensiometers that work according to this method.

In the present invention the interfacial tension is preferably determined using the duNouy Ring Method as described in "Introduction to Colloid and Surface Chemistry" by Ducan J. Shaw, third edition, page 68-69.

The present invention provides the advantages that the obtained delivery device can be designed to have a prolonged delivery time and a large amount of compound for release, while simultaneously having an improved release profile compared to prior art delivery devices.

Due to the method of the invention it is now possibly to provide a delivery device for delivering one or more chemical compounds where the release profile can be maintained within a desired and relatively small interval for a prolonged time. Simultaneously the production of the delivery device is very gentle to the chemical compound such that virtually any chemical compound can be incorporated into the delivery device.

Whereas it has in the prior art, as for example described in WO 2005/055972 been well known to incorporate chemical compound into an IPN system, only a small fraction of the chemical compound incorporated into the IPN of the prior art could be released.

According to the invention it has been found that the work of adhesion ($W_{hc}$) between the various materials of the delivery device is important for the release of the chemical compound and it has been found that by selecting the second polymer and the loading solvent such that the work of adhesion ($W_{hc}$) between the second polymer and the chemical compound during at least a part of the loading is above 0 J/m$^2$, i.e. is should be positive, it is now possible to release the chemical compound. The speed of the release can further be regulated by the selection of the work of adhesion i.e. the higher the work of adhesion between the second polymer and the chemical compound during loading, the faster the release will be.

In an embodiment of the invention the work of adhesion between the chemical compound and the second polymer during at least a part of the loading is as follows: 100 J/m$^2 \geq W_{hc} \geq 0$ J/m$^2$, preferably, 75 J/m$^2 \geq W_{hc} \geq 1$ J/m$^2$, such as 50 J/m$^2 \geq W_{hc} \geq 5$ J/m$^2$, such as 30 J/m$^2 \geq W_{hc} \geq 10$ J/m$^2$.

The phrase "at least a part of the loading" means herein a part where the major amount of the chemical compound is loaded. In most situations the "at least a part of the loading" includes essentially during the entire loading process optionally with exception of a start up period.

It has been found that adequate and optimal release profiles for most chemical compounds can be obtained by selecting the work of adhesion between the chemical compound and the second polymer within the mentioned intervals.

For obtaining an effective release it is generally desired that the work of adhesion between the chemical compound and the second polymer during the loading is at least about 10 J/m$^2$, and to ensure that the release is not too fast it is desired that that the work of adhesion between the chemical compound and the second polymer during the loading is less than about 100 J/m$^2$, more preferably less than about 100 J/m$^2$.

It has been found that if the work of adhesion between the chemical compound and the second polymer during the loading is very high such as more than about 50 J/m$^2$, or even more than about 50 J/m$^2$, the release may be too fast for most chemical compounds The size of the chemical compound also influences the release profile. Usually chemical compounds with relatively low molecule weight will be released faster than chemical compounds with larger molecule weight.

Where the chemical compound has a molecule weight of 200 or less it is normally desired that the work of adhesion between the chemical compound and the second polymer during the loading is between about 5 J/m$^2$ and about 50 J/m$^2$, more preferably is between about 10 J/m$^2$ and about 30 J/m$^2$.

Where the chemical compound has a molecule weight of above 200 is at least about 20 J/m$^2$, more preferably at least about 30 J/m$^2$.

In an embodiment where the chemical compound has a molecule weight of between 200 and 800 the work of adhesion between the chemical compound and the second polymer during the loading is advantageously between about 15 J/m$^2$ and about 100 J/m$^2$, more preferably is between about 20 J/m$^2$ and about 75 J/m$^2$.

The rubber may be any rubber including natural rubber and/or synthetic rubber, such as a vulcanized polymer of isoprene. For good compatibility it is desired in an embodiment that the rubber is silicone rubber.

In a preferred embodiment the first continuous polymer comprises at least 10%, such as at least 20%, such as at least 40%, such as at least 60% by mass of the first continuous polymer which has a backbone consisting of Si and O atoms or consisting of Si atoms. Such polymers are well known in the art and are generally accepted for use against human skin and mucosals. In an embodiment of the invention the first continuous polymer comprises poly(dimethyl siloxane), poly(methylphenyl siloxane), fluorosilicone rubber, silicone esters, polysiloxanes, polysilanes, polychlorosilanes, polyalkoxysilanes, polyaminosilanes, polysilanes, polydialkylsiloxanes, polysiloxanes containing at least one phenyl substituent, vinyl-functionalized silicone, partially or fully fluorinated silicone or a mixture of two or more of the mentioned silicones.

The term polysiloxane may include silicones but it is used herein in its broadest sense, i.e. any polymeric structure that contains repeating silicium-oxygen groups in the backbone, side chains or cross links regardless of the substitution on the silicium atom. The presence of certain organic groups attached to the silicium atom in silicone and polysiloxane binders moderates physical, mechanical and chemical properties, typically in an advantageous way.

The first continuous polymer may additionally comprise minor amounts of fillers and production additives which are usually present in polymers. The first continuous polymer is preferably at least partially vulcanized, such as up to a vulcanization degree (cross-linking degree) of at least 10%, such as at least 50%, such as at least 80% or wholly, such as at least 96%, such as at least 97%, such as at least 98%.

The first continuous polymer may for example be as the silicon substrate for an IPN as described in WO 2005/055972, US20100040870 and U.S. Pat. No. 7,687,585B2.

In one embodiment the first continuous polymer is a co-polymer of silicone-containing monomer, such as polydimethylsiloxane (a vinyl carbamate derivative of TRIS) co-polymerized with a hydrophilic monomer, such as N-vinyl pyrrolidone (NVP). This silicone material preferably has equilibrium water content (EWC) at 25° C. of about 20-40% by mass. However, generally it is desired that the first continuous polymer has a lower EWC than the second continuous polymer.

In a preferred embodiment the first continuous polymer has two main functions, namely to provide the delivery device with mechanical strength and stability and to act as a secondary reservoir for the chemical compound.

A first continuous polymer with a very high max. swelling may have an undesired low mechanical strength and stability.

The first continuous polymer preferably has a max. water swelling of about 40% by mass or less. Preferably the first continuous polymer has a max. water swelling of about 20% by mass or less. More preferably the first continuous polymer has a max. water swelling of about 10% by mass or less.

Generally it is desired that the first continuous polymer has a max. water swelling which in % by mass is lower than the maximal water swelling of the second polymer.

Max. water swelling means the maximal swelling of the polymer in question when soaked in water at pH 5 and at 25° C. until equilibrium water content. Unless other is specified, max. water swelling is given in % by mass of the polymer in question.

The water to be used in the determinations and tests as described herein is preferably Type III Laboratory-grade Water, e.g. provided by filtration with a Millipore filtration system.

In an embodiment of the invention, the water is replaced with artificial salvia.

The artificial salvia is prepared according to Macknight-Hane and Whitford formula (1992) with the following composition:
1 liter Type III Laboratory-grade Water
2 gram Methyl-P-hydroxybenzoate
10 g Sodium Carboxymethyl Cellulose
0.625 g KCL
0.059 g $MgCl_2.6H_2O$
0.166 g $CaCl_2.2H_2O$
0.804 g $K_2HPO_4$
0.326 $KH_2PO_4$
pH is adjusted to 6.75 using KOH.

In an embodiment of the invention the second polymer is a hydrogelable precursor i.e. a polymer which becomes a hydrogel upon soaking in water.

In an embodiment of the invention the second polymer is a hydrogel.

The second polymer may in principle be any matrix for water or saliva such as a hydrogel or a precursor therefore. The chemical compound will travel in the water/saliva to the surface of the delivery device for release to a selected site e.g. a site on skin or mucosals on a living human or animal.

The second polymer may for example be a homopolymer, preferably polymerised from an acrylate monomer or a vinyl polymer, more preferably n-vinyl pyrolidone (nVP), styrene; oxygen-, phenyl, amino and nitrogen-containing acrylic and methacrylic derivatives, e.g. acrylic esters, acrylic acids, methacrylic acid and -esters, alkyl and hydroxyalkyl acrylates and methacrylates; functionalized methacrylates such as 2-hydroxyethyl methacrylate (HEMA), glycerol monomethacrylate (GMMA), heptafluorobutyl acrylate (HFBA), 2-methacryloyloxyethyl phosphorylcholine (MPC) and [2-(methacryloyloxy)ethyl]-dimethyl-(3-sulfopropyl)-ammonium hydroxide (Betain); alkyl substituted acrylates and methacrylates such as methyl methacrylate (MMA), ethyl methacrylate (EMA), butyl methacrylate (BMA), dodecyl methacrylate (DMA), substituted β- and γ-lactones, lactic acid monomers; carbohydrides and fluorinated monomers, urethanes; mono- and di-functional alcohols; carboxylic acids; amines; isocyanates; epoxides; aromatics carrying alkyl group(s), sulfonated aromatics, aromatic resins, imidazol, imidazol derivatives; pyrazoles and/or quaternary ammonium monomers.

In a preferred embodiment the second polymer is a copolymer, preferably polymerised from monomers comprising silanes, e.g. tetraethylorthosilicate or tetraethoxysilane (TEOS), an acrylate monomer or a vinyl polymer, more preferably n-vinyl pyrolidone (nVP), styrene; oxygen-, phenyl, amino and nitrogen-containing acrylic and methacrylic derivatives, e.g. acrylic esters, acrylic acids, methacrylic acid and -esters, alkyl and hydroxyalkyl acrylates and methacrylates; functionalized methacrylates such as 2-hydroxyethyl methacrylate (HEMA), glycerol monomethacrylate (GMMA), heptafluorobutyl acrylate (HFBA), 2-methacryloyloxyethyl phosphorylcholine (MPC) and [2-(methacryloyloxy)ethyl]-dimethyl-(3-sulfopropyl)-ammonium hydroxide (Betain); alkyl substituted acrylates and methacrylates such as methyl methacrylate (MMA), ethyl methacrylate (EMA), butyl methacrylate (BMA), dodecyl methacrylate (DMA), substituted β- and γ-lactones, lactic acid monomers; carbohydrides and fluorinated monomers, urethanes; mono- and di-functional alcohols; carboxylic acids; amines; isocyanates; epoxides; aromatics carrying alkyl group(s), sulfonated aromatics, aromatic resins, imidazol, imidazol derivatives; pyrazoles and/or quaternary ammonium.

In a more preferred embodiment the second polymer is poly(2-hydroxyethyl methacrylate) (PHEMA).

PHEMA is a very stable hydrogel which furthermore is highly accepted for use in medical devices.

The second polymer can in principle be polymerized from any monomer to provide a hydrogel or a hydrogel precursor (i.e. a hydrogelable precursor).

Hydrogels are herein defined as cross-linked polymer networks that are insoluble in aqueous liquid solutions at pH values between 4 and 8 and are able to swell water such as at least about 10% by its own dry mass.

The traditional meaning of the term "gel" is that a gel is a three-dimensional cross-linked network. When a dry gel is placed in a solvent (e.g. water for hydrogels), the gel will swell the solvent e.g. up to several hundreds or even thousand times its own mass. The internal network structure may result from physical bonds (physical gels) or chemical bonds (chemical gels), as well as crystallites or other junctions that remain intact within the solvent.

Hydro gels are mostly fluid in composition and accordingly the mechanical strength of a hydrogel is usually relatively low.

Hydrogelable precursors are herein defined as polymers which upon cross-linking or additional-cross-linking become hydrogels.

In a preferred embodiment the second polymer has two main functions, namely to provide the delivery device with a good traveling medium for the chemical compound and to act as a primary reservoir for the chemical compound.

Accordingly the mechanical strength of the second polymer is not too important since the first polymer provides the mechanical strength. However, generally it is desired that the second polymer is a hydrogel.

In order for the second polymer not to bleed out of the first polymer, the second polymer should preferably be solid or have a high viscosity at 25° C. and 1 standard atmosphere (101.325 kPa), such as a dynamic viscosity of about 100 Pa*s or more, such as of about 200 Pa*s or more. Bleeding (the amount of second polymer released from the first polymer during storing at 25° C.) can be reduced or fully avoided by cross-linking of the second polymer.

To provide a good traveling medium for the chemical compound the second polymer should preferably have a high max. water swelling.

The second polymer preferably has a max. water swelling of about 10% by mass or more. Preferably the second polymer has a max. water swelling of about 20% by mass or more. More preferably the second polymer has a max. water swelling of from about 10% by mass to about 50% by mass. Particular preferred second polymers, such as PHEMA has a max. water swelling of about 40% by mass.

Generally it is desired that the second polymer has a max. water swelling which in % by mass is higher, such as 1.2 to 5 times higher than the max. water swelling of the first polymer.

The second polymer should preferably have a high swelling degree. The second polymer provides a matrix for the water/saliva through which the chemical compound migrates. Due to the high water content the second polymer is not stable in form and may disintegrate when subjected to various forces. However, the first polymer provides a scaffold and a mechanical protection for the second polymer.

In an embodiment of the invention the second polymer has a max. water swelling at 25° C. of about 10-10000% by mass of its dry mass, such as of about 20-5000% by mass of its dry mass, such as of about 20-500% by mass of its dry mass.

In preferred embodiments the max. water swelling of the second polymer is close to about 100% (i.e. about 50% by mass of the swelled second polymer at EWC is water and about 50% by mass is polymer).

In an embodiment of the invention the second polymer has a max. water swelling at 25° C. w/w of its dry mass which is higher than the max. water swelling at 25° C. w/w of the first continuous polymer.

In an embodiment of the invention the IP substrate has a max. water swelling at 25° C. of about 5-5000% by mass of its dry mass, such as of about 15-1000% by mass of its dry mass, such as of about 20-500% by mass of its dry mass, such as of about 40-100% by mass of its dry mass.

Generally is desired that the IP substrate comprises a continuous matrix of the first continuous polymer and a plurality of interpenetrating paths of the second polymer. The migrations of the chemical compound will be provided along the interpenetrating paths of the second polymer, and may be controlled by altering the amount of second polymer relative to the amount of the first polymer.

In an embodiment of the invention the IP substrate comprises a continuous matrix of the first polymer and a plurality of interpenetrating paths of the second polymer, the IP substrate has a surface and the plurality of interpenetrating paths of the second polymer coincides with said surface, whereby the chemical compound can be released via this surface.

The plurality of interpenetrating paths of the second polymer may be in the form of discrete paths, groups of paths or the paths may form a network. In the latter case the IP substrate is an Interpenetrating Polymer Network (IPN).

The term "paths" means domains provided by volumes of the swelled second polymer.

In one embodiment the plurality of interpenetrating paths of the second polymer may be in the form of groups of paths where groups of paths are interconnected with each other but not with paths of other groups of paths.

In one embodiment the plurality of interpenetrating paths of the second polymer may be in the form of discrete paths, where the main part of the paths is not interconnected.

An IP substrate with discrete paths or groups of paths may be provided by preparing a first continuous matrix of the first polymer, providing a desired pattern of microstructures in the first continuous matrix of the first polymer e.g. by a laser and filling the microstructures of the first continuous matrix of the first polymer with monomers for the second polymer followed by polymerization.

The IP substrate can be provided by the method as described in U.S. Pat. No. 7,687,585.

In an embodiment of the invention the IP substrate is provided by:
i) providing a first polymer composition,
ii) providing one or more monomers for a the second polymer,
iii) providing a solvent for the one or more monomers, preferably a $CO_2$ containing solvent,
iv) exposing the first polymer composition to the one or more monomers and the solvent optionally in liquid, supercritical or sub critical condition to precipitate monomer within the silicone polymer composition and
v) polymerizing the monomer to form an IPN and optionally cross-linking the second polymer.

In a preferred embodiment the IP substrate is or comprises an Interpenetrating Polymer Network (IPN).

The IPN may for example be produced by providing a virgin substrate of the first continuous polymer, subjecting the virgin substrate to an extracting treatment comprising extraction of residuals, swelling the extracted virgin substrate with a solvent comprising monomers and optionally a cross-linker for the second polymer and polymerizing the monomers to form the IPN.

The extraction is in an embodiment performed as the tempering described in WO 2006/045320 using liquid $CO_2$.

The amount of residual extracted is preferably between 0.5 and 15% by mass of the virgin substrate which is preferably silicone.

By selecting the virgin polymer and the amount of residuals extracted from the virgin substrate, the amount and structure of the network formed by the second polymer can be adjusted and thereby also the final release profile of the delivery device can be adjusted.

The more residual extracted, the more second polymer can be provided in the IPN, and it is believed that the more chemical compound can be loaded into the IP substrate. However, simultaneously—with high amount of second polymer—the length the chemical compound needs to travel along pathways of the network formed by the second polymer will be shorter, than in situations where the amount of second polymer is less and is distributed in a finer network. In principle for obtaining a long and substantially flat (same level of release per time unit for long time) release profile it is desired to have high amount of second polymer distributed in a fine network.

In an embodiment the virgin substrate is selected to have relatively low amount of extractable residual, such as up to about 3% by mass, such as from about 0.5 to about 2% of extractable residual, where the amount of extractable residual is determined by subjecting a 10 Ø, 1 mm thick virgin substrate to an extraction treatment using liquid $CO_2$ at 15° C. and 30 bar for 20 hours.

At least about 50% by mass, preferably at least about 75% by mass of the extractable residuals are extracted and the second polymer is provided as described above.

In an embodiment the IP substrate is an IPN in its whole structure (i.e. through out its thickness).

In an embodiment the IP substrate is an IPN in at least a part of the substrate, preferably in a surface part of the structure.

In order to have a good release it is desired that the IP substrate has at least about 1% of second polymer by dry mass of the total mass of the IP substrate, preferably the IP substrate has at least about 5%, such as at least about 10%, such as at least about 15%, such as at least about 20%, such as at least about 30% of second polymer by dry mass of the total mass of the IP substrate.

Preferably the mass amount of second polymer in the IP substrate is from about 1% to about 70% by mass of total mass of the dry IP substrate. If the amount of second polymer to first continuous polymer is high, such as above about 50% w/w (dry mass) the IP substrate may require that a supporting structure is used during loading in order for the IP substrate to maintain its structure in particular in situation where the swelling during loading is very high.

In order to obtain a delivery device with a long term release it is desired that the amount of first continuous polymer should be at least about 50% by mass of the dry mass of the IP substrate, such as preferably from about 70% by mass to about 80% by mass dry mass.

In a preferred embodiment the dry mass ration of first polymer to the second polymer is from about 80:20 to about 70:30, preferably about 75:25.

For obtaining an increased amount of the chemical compound in the delivery device released it has been found that the work of adhesion between the first continuous polymer and the chemical compound during the loading is relevant.

Therefore, in a preferred embodiment of the invention, the first continuous polymer and the loading solvent are selected such that the work of adhesion ($W_{sc}$) between the first continuous polymer and the chemical compound during at least a part of the loading is at least about 0 J/m², preferably $W_{sc} \geq 5$ J/m², such as $W_{sc} \geq 10$ J/m², such as $W_{sc} \geq 15$ J/m², such as $W_{sc} \geq 20$ J/m², such as $W_{sc} \geq 30$ J/m², such as $W_{sc} \geq 35$ J/m².

It is believed that some of the chemical compound will adhere to the first continuous polymer—e.g. at an interface between the first continuous polymer or on internal surfaces (interfacial surfaces in contact with liquid (water) that has been swelled) and the second polymer, some of the chemical compound will adhere to the second polymer and the remaining part of the chemical compound will be present as free compounds mainly in the second polymer—either dissolved in fluid with which the second polymer is swelled or as precipitate in the dried second polymer.

Independently of $W_{hc}$ in a given embodiment the work of adhesion ($W_{sc}$) between the first continuous polymer and the chemical compound during the loading is advantageously as described for the work of adhesion between the chemical compound and the second polymer during the loading described above relative to the molecule weight of the chemical compound.

For obtaining an effective release of the chemical compound from the first polymer to the second polymer it is generally desired that the work of adhesion between the chemical compound and the first polymer during the loading is at least about 10 J/m², more preferably at least 20 J/m²

To ensure a stable and flat release curve over a prolonged time it is desired that the work of adhesion ($W_{hc}$) between the chemical compound and the second polymer during the loading and the work of adhesion ($W_{sc}$) between the chemical compound and the first polymer during the loading are relatively close to each other, preferably with a difference of about 10 J/m² or less, more preferably with a difference of about 5 J/m² or less Where the chemical compound has a molecule weight of 200 or less it is normally desired that the work of adhesion between the chemical compound and the second polymer during the loading is between about 5 J/m² and about 50 J/m², more preferably is between about 10 J/m² and about 30 J/m².

Advantageously $W_{sc}$ is within the range of ±30 J/m² of $W_{hc}$. Preferably $W_{sc}$ is within the range of ±10 J/m² of $W_{hc}$.

In a preferred embodiment to ensure a high and constant release profile, $W_{sc}$ is from about the value of $W_{hc}$ to about $W_{hc}+20$ J/m² i.e. the release from the first polymer to the second polymer of the chemical compound is at least as fast as the release from the second polymer to a point of use.

If the loading is performed with a solvent that does not swell the first polymer, the chemical compound in the delivery device will mainly or totally be in the second polymer, some of the chemical compound will adhere to the second polymer and the remaining part of the chemical compound will be present as free compounds—either dissolved in fluid with which the second polymer is swelled or as precipitate in the dried second polymer, a minor part of the chemical compound will likely adhere to the first polymer in the interface between the first and the second polymer.

If the loading is performed with a solvent that does swell the first polymer—this is preferred—the chemical compound in the delivery device will be both in the first and in the second polymer either adhered to one or both of the first and the second polymer, dissolved in fluid with which the first and second polymer is swelled or as precipitate in the dried first polymer or the dried second polymer.

In an embodiment of the invention the work of adhesion between the chemical compound and the first continuous polymer during at least a part of the loading is as follows: 100 J/m² ≥ $W_{sc}$ ≥ 0 J/m², preferably, 75 J/m² ≥ $W_{sc}$ ≥ 1 J/m², such as 50 J/m² ≥ $W_{sc}$ ≥ 5 J/m², such as 30 J/m² ≥ $W_{sc}$ ≥ 10 J/m².

It has been found that adequate and optimal release profiles with release of high amounts of chemical compound in the delivery device can be obtained for most chemical compounds when selecting the work of adhesion between the chemical compound and the first polymer within the mentioned intervals.

The amount of chemical compound adhering to the first polymer, adhering to the second polymer and present as free chemical compound in the respective polymers can be regulated by a proper selection of work of adhesion, such that the work of adhesion for the chemical compound-first continuous polymer ($W_{sc}$) during the loading is higher than the work of adhesion between the chemical compound and the second polymer ($W_{hc}$) during loading.

In an embodiment of the invention, the work of adhesion for the chemical compound-first continuous polymer ($W_{sc}$) during at least a part of the loading is higher than the work of adhesion between the chemical compound and the second polymer ($W_{hc}$), such as at least about 5% higher, such as at least about 10% higher, such as at least about 20% higher, such as at least about 30% higher, such as at least about 40% higher, such as at least about 50% higher, such as at least about 60% higher than the work of adhesion between the chemical compound and the second polymer.

The amount of chemical compound loaded into the substrate can further be controlled by selecting the swelling degrees of the respective polymers.

If the first polymer is not swelled by the loading solvent and the loading solvent is swelling the second polymer only, substantially no chemical compound will be loaded into the first polymer, but some chemical compound will anyway adhere to surfaces of the first polymer.

In order for the first polymer to provide a good reservoir for the chemical compound it is preferred that the first polymer is at least slightly swelled by the loading solvent.

In an embodiment of the invention the first continuous polymer during at least a part of the loading is swelled with the loading solvent, preferably the relative swelling of the first continuous polymer by the loading solvent is at least about 0.2 times the relative swelling of the second polymer by the loading solvent, preferably the relative swelling of the first continuous polymer by the loading solvent is at least about 0.2 times, such as at least about 0.5 times, such as at least about 1 time, such as at least about 1.5 times, such as at least about 0.2 times the relative swelling of the second polymer by the loading solvent.

The term "relative swelling" means mass % of the solvent that is swelling the dry second polymer/first continuous polymer, in relation to the dry mass of the second polymer.

Dry mass of the second polymer/IP substrate is the mass obtainable by drying the second polymer/IP substrate at 50° C., 30% humidity air and standard atmospheric pressure until constant mass.

The amount of loading solvent that swells the silicone may preferably be kept relatively low, because chemical compound that is adhered in the first continuous polymer may be captured therein and not or only partly be released later on, whereas chemical compounds that are adhered to the first continuous polymer at the interface between the first continuous polymer and the second polymer to a much higher degree will be released when desired.

In one desired embodiment, the loading solvent comprises one or both of the compounds $N_2$ and $CO_2$. The most preferred solvent is a solvent comprising $CO_2$.

In an embodiment, the loading solvent comprises at least 50%, such as at least 75%, such as at least 90% by mass of one or more of the components selected from the group consisting of $CO_2$, and $N_2$, and $C_1$-$C_5$ hydrocarbons, the loading solvent preferably comprising at least 50%, such as at least 90% of $CO_2$.

The loading solvent preferably comprises $CO_2$ in liquid, subcritical phase or supercritical phase.

The fastest loading is obtained using supercritical $CO_2$ optionally in combination with a co-solvent. However, supercritical $CO_2$ loading requires a reactor for high pressure and such process can be relatively expensive. For that reason it is often desired to apply a sub critical loading or a fluidic $CO_2$ loading.

In one embodiment, the pressure during the loading is preferably well above 2 kg/cm$^{2'}$ such as at least 30 kg/cm$^2$, such as at least 40 kg/cm$^2$, such as between 40 and 500 kg/cm$^2$ such as between 50 and 300 kg/cm$^2$ such as between 60 and 200 kg/cm$^2$, such as between 70 and 150 kg/cm$^2$.

It should be understood that the pressure may vary during the loading e.g. so that the loading solvent (preferably comprising or even consisting essentially of $CO_2$) is changing state from liquid to supercritical or vice versa during the loading. Such pressure regulation may result in an even faster loading of the chemical compound.

The temperature at the loading is preferably at least 0° C., such as at least 10° C., such as at least 10° C., such as between 15 and 120° C., such as between 25 and 80° C.

In an embodiment, the solvent consists essentially of $CO_2$ and optionally a co-solvent. The critical points of a carbon dioxide are about 31.0° C. and 75.3 kg/cm$^2$, and it is referred to as being in a supercritical condition to be in the condition of having exceeded this and to have the in-between property of a liquid and a gas, i.e., the consistency near a liquid, and a diffusion coefficient near a gas. Moreover, although there is no clear definition, generally a subcritical state exists near the supercritical condition, i.e. about 50 kg/cm$^2$ or more and in about 25° C. or more, this condition is herein applied for a subcritical state. In one embodiment, it is thus desired that the pressure and temperature are selected so that the $CO_2$ is in its subcritical state during at least part of the exposing step.

In an embodiment of the invention the loading solvent comprises a co-solvent which in liquid phase can dissolve or disperse the chemical compound, the co-solvent is preferably water, an organic solvent or a combination thereof.

The organic solvent may for example comprise or be hexane, benzene, methanol, ethanol, chloroform, xylene, iso-butanol, propanol, acetone, acetonitrile, ethylene glycol or mixtures thereof.

In an embodiment of the invention, the loading solvent comprises an organic co-solvent selected from alcohols, such as EtOH, the loading solvent optionally comprises one or more chemical compounds in the form of fluids and or particles, such as buffers, surfactants, fragrances, dyes or flavors.

In one embodiment the loading solvent further comprises a surfactant preferably selected from the group of anionic, cationic, non-ionic and amphoteric surfactants, said impregnation solvent preferably comprising up to 5% by mass, such as between 0.001-50 grams of surfactant per kg loading solvent.

The chemical compound may in principle be any type of chemical compound or combinations of chemical compounds, which are compatible with the first and the second polymer. If the chemical compound becomes very large it may be difficult or time consuming to load the chemical compound into the substrate. Preferably the chemical compound should therefore have a molar mass of about 100000 g/mol or less.

In an embodiment of the invention, the chemical compound has a molar mass of up to about 90000 g/mol, such as up to about 50000 g/mol, such as up to about 10000 g/mol, such as up to about 5000 g/mol.

In a preferred embodiment the chemical compound has a molar mass of from about 50 g/mol to about 50000 g/mol. Generally the invention is highly beneficial in situations where the chemical compound has a molar mass of at least about 200 g/mol or more preferably at least about 200 g/mol, such as such as sulphamethizole with a molar mass of 270.333 g/mol.

Advantageously the chemical compound is not a salt. It has been found that where the first continuous polymer is silicone rubber (or simply called 'silicone'), the amount of releasable chemical compound when the chemical compound is a salt is low compared to when the chemical compound is not a salt. It appears that a part of the loaded salt is rather difficult to have released. Silicone rubber (polysiloxanes) differ from other polymers in that their backbones consist of Si—O—Si units unlike many other polymers that contain carbon backbones. The siloxane backbone unit Si—O has a bond length which is longer than the usually backbone unit bond length of C—C containing polymers and simultaneously the Si—O bond angle is larger i.e. about of 130°. It is believed that the negatively loaded 'O' of the Si—O bond has a strong electronegativity providing an attraction to the positively loaded metal ion of the dissolved salt, which result in that the metal ion will be more or less adsorbed to the silicone such that a layer of metal ion will be trapped along the interface between the hydrogel and the silicone.

Therefore where the chemical compound is a salt, it is preferred that the first continuous polymer is not silicone rubber. In the same way, where the first continuous polymer is silicone rubber it is preferred that the chemical compound is not a salt.

In a preferred embodiment the chemical compound is a drug. The term "drug" is to be construed to include any pharmaceutical, active compounds.

Examples of drugs which can be used with large advantages are as follows: Anticonvulsants, analgesics, antiparkinsons, antiinflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids sympathomimetics, parasympathomimetics, tranquilizers, urinary tract drugs, vaccines, vaginal drugs, vitamins, collagen, hyaluronic acid, non-steroidal anti-inflammatory drugs, angiotensin converting enzymes, polynucleotides, polypeptides, polysaccharides, nicotine, adreanal hormones and mixtures thereof.

In an embodiment of the invention, the drug is a drug for reducing pressure in the eyes.

In an embodiment the delivery device is for use as an implant or as part of an implant, such as an ear implant and the chemical compound is or comprises preferably one or more antibiotics and/or adreanal hormones.

The skilled person will appreciate that the delivery device of the invention can be produced for a large amount of applications and that the present invention opens up the prospects of a large number of new drug delivery devices.

However, the chemical compound can also be or include other types of compounds.

In an embodiment of the invention the chemical compound is or comprises stem cell(s), catalyst(s), nanoparticle(s) or combinations thereof.

In an embodiment of the invention the chemical compound is a compound for human nutrition, such as a vitamin, a protein and/or a mineral or a component comprising one or more of the before mentioned.

In an embodiment of the invention the chemical compound is a compound for microbiologic nutrition, such as $FeSO_4.7H_2O$, $ZnSO_4$, $KCl$, $MgSO_4$, $7H_2O$, $NaNO_3$, Glucose, NaCl, $K_2HPO_4$, $NH_4H_2PO_4$, $CaCl_2.2H_2O$, $FeCl_3.6H_2O$, $NaH_2PO_4$, $Na_2HPO_4$, $NaHCO_3$, $(NH_4)_2SO_4$ or mixtures comprising any of the mentioned.

In an embodiment of the invention the chemical compound is a fragrance compound, a flavor compound and/or a color compound (e.g. pigment and dyes).

In principle the opportunities are endless and the method and delivery device of the present invention opens up the prospect of a whole new type of delivery devices.

As mentioned above the delivery device can be loaded with more than one chemical compound. In an embodiment of the invention the method comprises loading the IP substrate with a plurality of chemical compounds simultaneously or in overlapping or separate steps.

In an embodiment of the invention the chemical compound has at least one hydrogen bond donor.

In an embodiment the delivery device is electric conductive. This may for example be provided by selecting the first continuous polymer to comprise intrinsically conducting polymers, such as Poly(p-phenylene vinylene) (PPV).

In an embodiment the delivery device is electric conductive provided by incorporating conductive molecules or particles, such as silver powder, carbon black and metal dust, into the first continuous polymer. The electrical conductivity may be used to control and/or trigger the release of chemical compound from the delivery device.

In an embodiment the delivery device is an electric conductive provided by selecting the chemical compound to be an electric compound such as a loaded ion. Such device may be for use in battery wherein the electric conductive unit is electric conductive because the chemical compound is an electric loaded compound dissolved in water in, such as silver ions.

In an embodiment the delivery device is for use as a filter e.g. an electric filter.

In an embodiment the IP-substrate is in form of relatively small particles, such as with a size of about 100 microns or less, such as of about 10 microns or less or of sized which are normally acceptable in paint. The particles may alternatively be provided by granulating after the chemical compound has been loaded. In this embodiment the chemical compound may for example be a compound that suppresses marine growth, such as a biocide, an antifouling effective compound such as a compound inhibiting growth of barnacles. The particles may be mixed into a paint or may in other way be arranged in a dispersion which can be applied to marine equipments such as a vessel.

The loading of the IP substrate with the chemical compound may for example be provided by arranging the IP substrate in a reaction chamber and at least partially swelling the second polymer with the loading solvent under conditions wherein at least a part of the loading solvent is in a sub-critical phase or supercritical phase.

In an embodiment of the invention the loading of the IP substrate with the chemical compound comprises swelling the second polymer with the loading solvent comprising the chemical compound at a temperature of at least about 10° C. and at elevated pressure, preferably a pressure of at least about 1000 kPa, such as at least about 4000 kPa, such as at least 8000 kPa, such as at least about 200 kPa.

In an embodiment of the invention the loading of the IP substrate with the chemical compound comprises swelling the second polymer with the loading solvent comprising the chemical compound at a temperature of at least about 20° C. and at elevated pressure, preferably a pressure of at least about 4000 kPa, such as at least 8000 kPa, such as at least about 200 kPa and wherein the loading solvent comprises $CO_2$.

The time required for a desired loading can easily be found by a few routine experiments. In an embodiment of the invention the loading of the IP substrate with the chemical compound comprises swelling the second polymer with the loading solvent comprising the chemical compound for a period of at least about 30 minutes, such as at least about 1 hour, such as at least about 2 hours, such as at least about 4 hours, such as at least about 8 hours, such as at least about 10 hours, such as at least about 16 hours.

In an embodiment of the invention the loading of the IP substrate with the chemical compound comprises swelling the second polymer with the loading solvent comprising the chemical compound at an elevated pressure for a preselected period, followed by lowering the pressure to about one standard atmosphere.

The loading solvent should be selected such that the loading solvent is not dissolving or degenerating the first continuous polymer or the second polymer during loading of the chemical compound.

In an embodiment of the invention the loading solvent comprises a first fluid and a second fluid, wherein the first fluid during loading is in a sub-critical stage or supercritical stage and the second fluid is or comprises a co-solvent for the chemical compound, which in liquid stage can dissolve the chemical compound.

The IP substrate will normally be loaded with the chemical substrate in a reactor. In principle, the IP substrate, the solvent in the form of one or more fluids and the chemical compound(s) may be fed to the reactor in any order. Normally it will be most convenient to place the IP substrate in the reactor, close the reactor and thereafter feed solvent and chemical compound in any order.

The temperature may be adjusted prior to, simultaneously with and/or after the fluid or fluids providing the solvent has been feed and/or simultaneously with and/or after the chemical compound(s) has/have been fed.

The pressure may be adjusted prior to, simultaneously with and/or after the fluid or fluids providing the solvent has been feed and/or simultaneously with and/or after the chemical compound(s) has/have been fed.

For loading large amounts of chemical compound it is preferred that the method comprises dissolving the chemical compound in the second fluid, the second fluid is preferably at least about 20% saturated with the chemical compound, such as at least about 40% saturated, with the chemical compound at the loading temperature but prior to loading.

In an embodiment of the invention the method comprises
arranging the IP substrate in a reactor
feeding the first fluid to the reactor
feeding the second fluid with the dissolved chemical compound to the reactor
swelling the IP substrate with the first fluid and at least a part of the second fluid of the loading solvent to load the IP substrate with the chemical compound.

The order of feeding the first fluid and the second fluid with the dissolved chemical compound to the reactor can be reversed or alternatively the first fluid and the second fluid with the dissolved chemical compound can be fed to the reactor partly (overlapping in time) or fully simultaneously.

The first and the second fluids are preferably miscible at the loading conditions.

In an embodiment of the invention the feeding of the second fluid with the dissolved chemical compound to the reactor is performed by placing the second fluid with the dissolved chemical compound directly in the reactor or by introducing the second fluid with the dissolved chemical compound in one step into the reactor prior to initiating the loading of the IP substrate with the chemical compound.

In an embodiment of the invention the feeding of the second fluid with the dissolved chemical compound to the reactor is performed by continuously or step wise feeding the second fluid with the dissolved chemical compound into the reactor, where the feeding continues during at least a part of the loading of the IP substrate with the chemical compound.

The feeding of the first fluid and optionally an inert gas into the reactor may be performed continuously or step wise to raise the pressure in the reactor to a pressure sufficiently to swell the IP substrate with the first fluid. Preferably the pressure is raised to at least about 4000 kPa and optionally the temperature is simultaneously raised to provide that the first fluid is in its sub-critical or critical phase.

As indicated above the pressure may be pulsated during at least a part of the loading of the IP substrate with the chemical compound. The pulsating may for example comprise a repeating variation of pressure of 100-1000 kPa, e.g. with a repeating rate of one pulse per 5 to 120 minutes.

In order not to waste chemical compound the IP substrate is preferably provided with a selected shape prior to the loading with the chemical compound, wherein the selected shape is the shape it will have in the delivery device, the shape may optionally be provided by casting, molding, cutting, pressing, granulating or mixtures thereof.

In an alternative embodiment or in addition to the embodiment with the pre shaping, the method further comprises shaping the loaded IP substrate to obtain the delivery device, the shaping comprises cutting, pressing, granulating, or mixtures thereof.

The method may further comprise combining the loaded IP substrate or the loaded and shaped IP substrate with additional element or elements to obtain the final delivery device, the additional element or elements comprise a carrier patch, a non-stick film/net, an adhesive, a support element, a coating or combinations thereof.

In a preferred embodiment the loaded IP substrate or the loaded and shaped IP substrate is combined with a top coating e.g. by grafting.

Examples of delivery devices which could be produced by the method of the invention comprise the following:
a baby nipple for adding pharmaceuticals during feeding, teething devices;
a catheter or shunt for any body fluid (urine, blood, excess water);
a drug delivery patch;
a nicotine patch;
a wound care product;
a surgical film;
a prophylactic device, such as a condom, a glove or a intravenous bag;
a contact lens;
an implant;
a diagnostic device;

After the loading the delivery device may for example be coated. The preferred coating depends on the type and purpose of the delivery device. The skilled person will know such different types of coatings.

In a preferred embodiment the delivery device is coated with a muco adhesive, such as proteins, carbohydrates, glycoproteins, and mucopolysaccharides Mucoadhesion coatings are well known in the art of drug delivery systems. Mucoadhesive drug delivery system prolongs the residence time of the dosage form at the site of application or absorption and facilitates an intimate contact of the dosage form with the underline absorption surface and thus contributes to improved and/or better therapeutic performance of the drug. The mucoadhesive coated delivery device may e.g. be for oral, buccal, nasal, rectal and/or vaginal application.

In an embodiment the method of the invention comprises producing a delivery device suitably for treatment of Cutaneous leishmaniasis (OWCL) which is a world wide disfiguring and stigmatising disease, caused by a parasitic infection transmitted by sand flies.

Cutaneous leishmaniasis is characterized by skin lesions (open or closed sores), which typically develop within several weeks or months after exposure. They typically progress from small papules to nodular plaques, and eventually lead to open sores with a raised border and central crater (ulcer), which can be covered with scales or crust. The lesions can last for months or years and typically result in scarring.

Heretofore Cutaneous leishmaniasis has typically been treated with intravenous or intramuscular administrated drugs.

The delivery device of the invention for treatment of Cutaneous leishmaniasis provides a new and advantageous treatment of Cutaneous leishmaniasis. The delivery device of the invention for treatment of Cutaneous leishmaniasis is advantageously shaped as patches which can be arranged to and optionally adhered to cover the skin lesions for release to the lesions.

The chemical compound or compounds loaded into the delivery device for treatment of Cutaneous leishmaniasis is advantageously one or more of Sodium stibogluconate (pentostam) N-Methylglucamine antimonate and Amphotericin The invention also comprises a delivery device obtainable by the method of the invention.

The delivery device for delivering a chemical compound comprises an IP substrate comprising a first continuous polymer comprising silicone, a second continuous polymer comprising second polymer and the chemical compound arranged to be released from the delivery device upon contact with aqueous liquid or moisture, wherein a part of the chemical compound is adhered to the first continuous polymer, a part of the chemical compound is adhered to the second polymer and the remaining part of the chemical compound is present as free compound in the first and second polymer dissolved or as crystals (precipitated form). Preferably about 50 mol % or less of the releasable chemical compound in the delivery device is present as free compound in the second polymer, such as about 30 mol % or less, such as about 20 mol % or less of the releasable chemical compound in the delivery device is present as free compound in the second polymer.

The total amount of chemical compound in the delivery device is determined by allowing 1 g (dry mass) of the delivery device to swell in a surplus of artificial salvia (e.g. 0.2 l) under stirring for 1 week at 25° C. and 1 standard atmosphere. The amount of chemical compound released to the water defines the releasable amount of chemical compound.

The amount of chemical compound present as free compound in the second polymer is determined by allowing 1 g (dry mass) of the delivery device to swell in a surplus of artificial salvia under stirring for 30 minutes at 25° C. and 1 standard atmosphere. The amount of chemical compound released to the artificial salvia defines the amount of chemical compound present as free compound in the second polymer.

The artificial salvia is as described above.

The delivery device for delivering a chemical compound preferably comprises an IP substrate comprising a first continuous polymer comprising silicone, a second continuous polymer comprising the second a polymer and the chemical compound arranged to be released from the delivery device upon contact with aqueous liquid or moisture, wherein at least about 50 mol % or less of the chemical compound in the delivery device requires an energy of 30 J/mol or less to be released, preferably at least about 50 mol % or less of the chemical compound in the delivery device requires an energy of about 10 J/mol or less, such as of about 5 J/mol or less, such as of about 2 J/mol or less to be released.

In a preferred embodiment the delivery device has a release profile of the chemical compound when applied in standard test (1 g of delivery device in a surplus of artificial salvia (e.g. 0.2 l), stirring at 25° C. and 1 standard atmosphere), which release profile in a period of at least about 5 hours, preferably at lease about 10 hours, preferably at least about 15 hours, preferably at least about 24 hours maintains a release amount of at least 50% by mol of an initial maximum release, determined as the average release during the first 30 minutes.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

All features of the inventions including ranges and preferred ranges can be combined in various ways within the scope of the invention, unless there are specific reasons not to combine such features.

EXAMPLES

The invention will be explained more fully below in connection with a preferred embodiment.

Some preferred embodiments have been shown in the foregoing, but it should be stressed that the invention is not limited to these, but may be embodied in other ways within the subject-matter defined in the following claims.

Example 1

An interpenetrating polymer substrate (IP substrate) was produced comprising a first continuous polymer of silicone (PDMS) and a second polymer of PHEMA hydrogel interpenetrating in the first polymer.

A 16 ml custom made stainless steel high-pressure reactor (Abeto, Denmark) was loaded with 4.0 ml ethanol, 2000 µL HEMA (2-hydroxyethyl methacrylate) and 60 µL EGDMA (ethyleneglycol dimethacrylate) and 15 discs in the given order. Discs (Ø 10 mm) were stamped out from a 1 mm silicone sheet. The silicone sheet was injection molded Elastosil LR3003 (10 Shore A) silicone elastomer supplied by Wacker Silicones (Germany). The reactor was closed and pressurized with $CO_2$ to approximately 56 bars at room temperature and heated to 75° C. When the temperature approached 75° C., $CO_2$ was added the reactor to approximately 200 bars. After three hours of impregnation 500 µL 0.15 M DEPDC (diethyl peroxydicarbonate) in hexane solution and $CO_2$ was added to the reactor to ensure a polymerization pressure of approximately 300 bars. After two hours of polymerization the reactor was allowed to return to ambient temperature before the pressure was slowly decreased. The IPNs were cleaned in ethanol. This procedure ensured a PHEMA content of about 17-30% by mass.

The example was repeated with silicone discs of up to 5 mm in thickness.

Example 2

Loading of Ceragenin CSA-13

6 IPN discs (010 mm, thickness 1-2 mm) obtained from Example 1 and with about 20% PHEMA (total mass about 1.3266 g) was loaded with about 500 mg Ceragenin CSA-13. The loading solvent was 2.00 ml 99.8% EtOH supplied by Merck (Germany) and N48 $CO_2$ (supplied by Air Liquid Denmark A/S (Denmark)). The Ceragenin CSA-13 was initially dissolved in the 2.00 ml 99.8% EtOH and injected into a reactor of 16 ml comprising the discs. The pressure was raised to about 300 bars by injecting $CO_2$ and the temperature was raised to about 75° C. The discs were treated at this pressure and temperature under stirring (1100 rpm) for 21 hours and 50 minutes, where after the pressure was reduced, the discs were withdrawn and allowed to cool down.

It was observed that a large amount of the Ceragenin CSA-13 had been loaded into the discs and it is expected that the major part of the loaded Ceragenin CSA-13 will be releasable from the delivery device. Test has shown that the Ceragenin CSA-13 can be released in sufficient amounts to provide a significant microbiological effect.

Example 3

Loading of Sulfamethizole 2.5 g sulfamethizole (Unikem) was mixed with 60 ml sodium thiosulfate solution (12 ml 0.1 M was diluted to 60 ml using deionized water).

Drug loading was performed by placing 10 discs obtained from Example 1 in a 16 ml reactor. 2.00 ml of the above sulfamethizole mixture and 2.00 ml 99.8% EtOH supplied by Merck (Germany) was fed to the reactor. The discs were kept under stirring during the treatment time. The pressure in the reactor was initially raised to about 100 bars and with a temperature of about 44° C. Thereafter the temperature was raised to 75° C. and the pressure increased to 300 bars with $CO_2$ (N48 $CO_2$ supplied by Air Liquid Denmark A/S). After a loading time of approximately 16 hours the pressure was slowly decreased and the discs were withdrawn.

It was found that the major amount of sulfamethizole loaded into the discs would be released when soaked in phosphate buffer solution at pH 4.5 over a period of about 14 days.

Example 4

Loading of Miconazole Test 1

Loading of discs with and without pHEMA using scCO2:
a) 10 PDMS (Polydimethylsiloxane) (silpuran 6000/40 supplied by Wacker) discs within the same mass range were used per high pressure vessel for loading drug into PDMS. 10 IPNs discs of similar size and shape as the PDMS discs (PDMS loaded with about 20% by mass of PHEMA as in Example 1) were placed in each high pressure vessel for loading drug into the IPN discs.
b) Approximately 1 g of miconazole nitrate was added to each high pressure vessel.
c) The reactors were properly closed and placed in water baths with stirring at 75° C. The reactors were then coupled to a $scCO_2$ system. $scCO_2$ was applied at 350 bars until the pressure inside the reactors also reached 350 bars. The pressure remained at 350 bars throughout the procedure. The reaction was left for equilibration for 2 hours.
d) The pressure was released, and the discs loaded with miconazole nitrate were gently cleaned with ethanol, and stored protected from light.

It was observed that the amount of miconazole nitrate releasable from the IPN discs was much higher than the amount releasable from the PDMS discs.

Example 5

Loading of Miconazole Test 2

Loading of PDMS discs with and without pHEMA using $scCO_2$ and methanol:
a) 10 PDMS (Polydimethylsiloxane) discs within the same mass range were used per high pressure vessel for loading drug into PDMS. 10 IPNs discs of similar size and shape as the PDMS discs (PDMS loaded with about 20% by mass of PHEMA as in Example 1) were placed in each high pressure vessel for loading drug into the IPN discs.
b) 10 ml of the supernatant of a centrifuged saturated solution of miconazole nitrate in methanol was added to each high pressure vessel.
c) The reactors were properly closed and placed in water baths with stirring at 75° C. The reactors were then coupled to a $scCO_2$ system. $scCO_2$ was applied at 350 bars until the pressure inside the reactors also reached 350 bars. This pressure was maintained throughout the procedure. The reaction was left for equilibration for 2 hours.
d) The pressure was released, and the discs loaded with miconazole nitrate were gently cleaned with ethanol, and stored protected from light.

It was observed that the amount of miconazole nitrate releasable from the IPN discs was much higher than the amount releasable from the PDMS discs.

Example 6

Loading of Silver Lactate 800 mg IPN (18% PHEMA) obtained as described in Example 1 was introduced into a 16 ml reactor together with 200 mg silver lactate, 2.00 ml 99.9% EtOH (Merck) and pressure was raised using $CO_2$ (N48) to 300 bars and the temperature was set to 75° C. The treatment was continued for 24 hours under stirring of the IPN.

1.4 g IPN (18% PHEMA) obtained as described in Example 1 was introduced into a 16 ml reactor together with 200 mg silver lactate, 1.6 ml 99.9% EtOH (Merck)) and pressure was raised using $CO_2$ (N48) to 100 bars and the temperature was set to 75° C. The treatment was continued for 24 hours under stirring of the IPN.

Example 7

Loading of Surfactants 30 g IPN (18% PHEMA) obtained as described in Example 1 was introduced into a 1 l reactor together with 5 ml demineralized water and 4.3 ml codamol GTCC. Pressure was raised using $CO_2$ (N48) to 70 bars and the temperature was set to 15° C. The treatment was continued for 1 hour under stirring of the IPN.

30 g IPN (18% PHEMA) obtained as described in Example 1 was introduced into a 1 l reactor together with 5 ml demineralized water and 422 ml Gradamol PC. Pressure was raised using CO2 (N48) to 70 bars and the temperature was set to 15° C. The treatment was continued for 1 hour under stirring of the IPN.

Example 8

Loading of Dye

In every batch 1-2 discs from Example 1 were cut and put in a reactor. 1-2 g of dye was added. The reactor was then filled with 3 liters of $CO_2$ (N48). The pressure was about 43 bars and the temperature 18° C. No additives were used. The treatment was carried out for 1 h. After the treatment the discs were washed with solvent (acetone) to remove excess dye.

| Batch | Dyes used: |
|---|---|
| A | Blue S0509B |
| B | Oracet yellow ghs |
| C | Oracet red BG |

Example 9

Loading of Fragrance

In every batch 1-2 discs from Example 1 were cut and put in a reactor. 0.5-2 g of fragrance was added. The reactor was then filled with $CO_2$ (N48) to a pressure of 70 bars and the temperature was set to 10° C. In some batches citronella oil was added, in other batches no additives were used. The treatment was carried out for 30-60 minutes. After the treatment the discs were washed with solvent (acetone) to remove excess fragrance.

| Batch | Fragrance | Additive |
|---|---|---|
| A | Cappuccino Test ID: 070906AJ0001 | |
| B | Cappuccino Test ID: 070907AJ0002 | |
| C | Coffee Test ID: 070910AJ0003a | 1% (w/w) Citronella of silicone rubber mass |
| D | Coffee Test ID: 070910AJ0003b | 3% (w/w) Citronella of silicone rubber mass |

Example 10

Loading of Kitotifen Fumarate 40 identical IPN contact lenses were obtained as described in WO 2008/052568 Example 1. 10 contact lenses had a total mass of 235.4 mg.

200 mg kitotifen fumarate, 2 ml 99.9% EtOH, and 10 of the above contact lenses were put in a reactor and treated with $CO_2$ (N48) under stirring according to the below scheme.

| Batch | Pressure Bars | Temperature ° C. | CO2 state | Treatment time Hours |
|---|---|---|---|---|
| A | 80 | 35 | Near supercritical (subcritical) | 5 |
| B | 300 | 75 | Supercritical | 1 |
| C | 100 | 10 | Liquid | 3 |
| D | 60 | 25 | Liquid/gas | 20 |

The release of kitotifen from the samples to a PBS-buffer was measured by UV-spectroscopy and compared with the release from samples loaded in PBS-buffer.

Example 11

Determination of Work of Adhesion

At 1 bar and 25° C. the respective work of adhesion between sulfamethizole and the two polymers PDMS and PHEMA of the IPN of Example 1 was determined with respectively EtOH and water as loading solvents.

The results were as follows

| Loading solvent | Work of adhesion Wsc (J/m$^2$) s = PDMS c = sulfamethizole | Work of adhesion Whc (J/m$^2$) h = PHEMA c = sulfamethizole |
|---|---|---|
| Water | 57.7309 | 38.3326 |
| EtOH | 6.3434 | 3.8908 |

Work of adhesion between sulfamethizole and the two polymers PDMS and PHEMA of the IPN of Example 1 was determined with varying volume fractions of EtOH in a loading solvent of EtOH and $scCO_2$.

The determination was determined at 300 bars and 75° C.

| ETOH part of loading solvent | scCO$_2$ part of loading solvent | Work of adhesion Wsc (J/m$^2$) s = PDMS c = sulfamethizole | Work of adhesion Whc (J/m$^2$) h = PHEMA c = sulfamethizole |
|---|---|---|---|
| 0.0000 | 1.0000 | 14.1969 | 29.8588 |
| 0.0625 | 0.9375 | 11.2585 | 25.3418 |
| 0.1250 | 0.8750 | 8.714 | 21.2182 |
| 0.1875 | 0.8125 | 6.5641 | 17.4885 |
| 0.2500 | 0.7500 | 4.8092 | 14.1531 |
| 0.3125 | 0.6875 | 3.4498 | 11.2126 |
| 0.3750 | 0.6250 | 2.4864 | 8.6675 |
| 0.4375 | 0.5625 | 1.9195 | 6.5181 |
| 0.5000 | 0.5000 | 1.7497 | 4.7652 |
| 0.5625 | 0.4375 | 1.9773 | 3.4091 |
| 0.6250 | 0.3750 | 2.6029 | 2.4503 |
| 0.6875 | 0.3125 | 3.6271 | 1.8894 |
| 0.7500 | 0.2500 | 5.0502 | 1.7267 |
| 0.8125 | 0.1875 | 6.8727 | 1.9629 |
| 0.8750 | 0.1250 | 9.0953 | 2.5985 |
| 0.9375 | 0.0625 | 11.7183 | 3.6338 |
| 1.0000 | 0.0000 | 14.7422 | 5.0694 |

The results are shown in the table above.

Example 12

Loading of Silicone without Hydrogel

A silicone disc (Ø 10 mm) was stamped out from a 1 mm silicone sheet. The silicone sheet was injection molded Elastosil LR3003 (10 Shore A) silicone elastomer supplied by Wacker Silicones (Germany). The disc was subjected to residual extraction treatment for 32 hours in liquid $CO_2$ at approximately 30 bars and 15° C. About 10% by mass of the silicone was extracted.

Loading with Fluorescein in Supercritical $CO_2$

The disc was introduced into a 2.65 ml reactor together with 2.5 ml fluorescein solution in water (0.01 mg fluorescein per ml), pressure was raised using CO2 (N48) to 300 bars and the temperature was set to 25° C. The treatment was continued for 2-24 hours under stirring of the IPN.

The fluorescein treated disc was studied in a laser scanning confocal microscope (LSCM) and no loading of fluorescein could be observed.

Example 13

Production of an IPN Substrate

An interpenetrating polymer substrate (IP substrate) was produced comprising a first continuous polymer of silicone (PDMS) and a second polymer of PHEMA hydrogel interpenetrating in the first polymer.

A silicone disc (Ø 10 mm) was stamped out from a 1 mm silicone sheet. The silicone sheet was injection molded Elastosil LR3003 (10 Shore A) silicone elastomer supplied by Wacker Silicones (Germany). The disc was subjected to residual extraction treatment for 32 hours in liquid $CO_2$ at approximately 30 bars and 15° C. About 10% by mass of the silicone was extracted.

A 2.65 ml high-pressure reactor was loaded with 984 µl 99.9% EtOH (Merck), 100 µL HEMA and 16 µL EGDMA and the silicone disc in the given order. The reactor was closed and pressurized with $CO_2$ to approximately 50 bars at room temperature and heated to 75° C. When the temperature approached 75° C., $CO_2$ was added to the reactor to approximately 200 bars. After three hours of impregnation 50 µL 0.15 M DEPDC in hexane solution and $CO_2$ was added to the reactor to ensure a polymerization pressure of approximately 300 bars. After 18 hours of polymerization the reactor was allowed to return to ambient temperature before the pressure was allowed to return to ambient temperature before the pressure was slowly decreased.

Fluorescein Loading of IPN Substrate in Water at Ambient Pressure

The disc was placed in an aqueous solution with 0.02 mg/ml fluorescein at 25° C. and ambient pressure for two weeks in order to reach an equilibrium water content.

The fluorescein treated IPN substrate was studied in a laser scanning confocal microscope (LSCM) at different times during the loading and it could be observed that there was a diffusion gradient into the samples which increased in depth as a function of time.

Example 14

Production of an IPN Substrate

An interpenetrating polymer substrate (IP substrate) was produced as in example 13.

Fluorescein Loading of IPN Substrate in Water in Supercritical CO2

The disc was introduced into the 2.65 ml reactor together with 2.5 ml fluorescein solution in water (0.01 mg fluorescein per ml), pressure was raised using $CO_2$ (N48) to 300 bars and the temperature was set to 25° C.

The treatment was continued for 2 hours under stirring of the IPN.

The fluorescein loaded IPN was studied in a laser scanning confocal microscope (LSCM) and it was observed that fluorescein was loaded into the IPN substrate to a depth of about 35-40 µm. The fluorescein was distributed with a homogeneous background distribution comprising a fine network and with domain of higher concentration. The domains of higher concentration of fluorescein were interconnected by the fine network and the fine network was stretching to the surface of the IPN disc. The concentration of fluorescein in the network domains was significantly higher than the background concentration of fluorescein.

Example 15

Production of an IPN Substrate

An interpenetrating polymer substrate (IP substrate) was produced as in example 13.

Fluorescein Loading of IPN Substrate in Water+EtOH in Supercritical CO2

The IPN substrate was introduced into the 2.65 ml reactor together with 1 ml fluorescein solution in water (0.01 mg fluorescein per ml) and 1 ml 99.9% EtOH (Merck), pressure was raised using $CO_2$ (N48) to 300 bars and the temperature was set to 25° C.

The treatment was continued for 2 hours under stirring of the IPN.

The fluorescein loaded IPN was studied in a laser scanning confocal microscope (LSCM) and it was observed that fluorescein was loaded into the IPN substrate to a depth of about 60-70 µm. Also here it was observed that the fluorescein was distributed with a homogeneous background distribution comprising a fine network and with domain of higher concentration. The domains of higher concentration of fluorescein were interconnected by the fine network and the fine network was stretching to the surface of the IPN disc.

Example 16

Production of IPN Substrate 5 silicone discs (Ø 10 mm) were stamped out from a 2 mm silicone sheet. The silicone sheet was injection molded Silpuran 6000 (40 Shore A) silicone medical grade elastomer supplied by Wacker Silicones (Germany). The disc was subjected to residual extraction treatment for 2 hours in liquid $CO_2$ at approximately 30 bars and 15° C. About 1% by mass of the silicone was extracted.

A 16 ml high-pressure reactor was loaded with 4 ml 99.9% EtOH (Merck), 2.00 ml HEMA and 60 µL EGDMA and the silicone discs in the given order. The reactor was closed and pressurized with $CO_2$ to approximately 50 bars at room temperature and heated to 75° C. When the temperature approached 75° C., $CO_2$ was added to the reactor to approximately 250 bars. After 20 minutes of impregnation 500 µL 0.15 M DEPDC in hexane solution and $CO_2$ was added to the reactor to ensure a polymerization pressure of approximately 360 bars. After 2.5 hours of polymerization the reactor was allowed to return to ambient temperature before the pressure was slowly decreased. The IPNs were cleaned in ethanol.

Fluorescein Loading of IPN Substrate in Water+EtOH in Supercritical CO2

One of the IPN substrates was introduced into a 2.65 ml reactor together with 1 ml fluorescein solution in water (0.02 mg fluorescein per ml) and 1 ml 99.9% EtOH (Merck), pressure was raised using $CO_2$ (N48) to 300 bars and the temperature was set to 25° C.

The treatment was continued for 2 hours under stirring of the IPN.

The fluorescein loaded IPN was studied in a laser scanning confocal microscope (LSCM) and it was observed that the fluorescein was homogeneously distributed in a fine network. It appeared that the IPN did not comprise domains of higher concentration as the loaded IPN in examples 14 and 15. It is believed that due to the IPN of the medical grade silicone (Silpuran 6000) the hydrogel is distributed in a much finer network that when using non-medical silicone, such as Elastosil LR3003. Due to the very fine distribution of the network, high concentration domains cannot be observed.

It is anticipated that by selecting the structure and fineness degree (determined by the cross-linking homogeneity of the PDMS—substrate material) of the hydrogel network in the silicone substrate, the release profile can be adjusted accordingly. A very fine network may provide that the chemical compound in the fine structure far from the surface of the IPN will have to travel relatively far in the hydrogel. This effect may be used to provide a desired release profile, such as a long and relatively stable release profile. Also it is expected that this effect can be used to provide a desired release profile where high concentrations of hydrogel can function to prolong the effective diffusion path and hence prolong the release.

Example 17

Loading of Sodium Stibogluconate (Pentostam)

2.5 ml of a Sodium stibogluconate solution with a concentration of 10 mg/ml and using demineralized water is prepared.

3 IPN disks prepared according to example 1, having 25 mass % HEMA, and a diameter of 10 mm and a thickness of 2 mm is obtained.

Drug loading is performed by placing the 3 discs in a 2.5 ml reactor. TT reactor is filled up with the above Sodium stibogluconate solution (about 2.5 ml). The discs are (optional) kept under stirring during the treatment time. The pressure in the reactor is raised to about 300 bars using $CO_2$ (N48 $CO_2$ supplied by Air Liquid Denmark A/S) and with a temperature of about 5° C. After a loading time of 4-24 hours the pressure is slowly decreased and the discs are withdrawn.

Example 18

Loading of N-Methylglucamine Antimoniate 2.5 ml of a N-Methylglucamine antimoniate solution with a concentration of 10 mg/ml and using 99.8% EtOH supplied by Merck (Germany) is prepared.

3 IPN disks prepared according to example 1, having 25 mass % HEMA, and a diameter of 10 mm and a thickness of 2 mm is obtained.

Drug loading is performed by placing the 3 discs in a 2.5 ml reactor. About 2.5 ml of the above N-Methylglucamine antimoniate solution is fed to the reactor (the reactor is filled up with the N-Methylglucamine antimoniate solution). The discs are kept under stirring during the treatment time. The pressure in the reactor is initially raised to about 100 bars using $CO_2$ (N48 $CO_2$ supplied by Air Liquid Denmark A/S) and with a temperature of about 45° C. Thereafter the temperature is raised to about 75° C. and the pressure is increased to 300 bars using further $CO_2$. After a loading time of approximately 3 hours the pressure is slowly decreased and the discs are withdrawn.

Example 19

Loading of Amphotericin 2.5 ml of an Amphotericin solution with a concentration of 10 mg/ml and using DMSO is prepared.

3 IPN disks prepared according to example 1, having 25 mass % HEMA, and a diameter of 10 mm and a thickness of 2 mm is obtained.

Drug loading is performed by placing the 3 discs in a 16 ml reactor. 2.5 ml of the above Amphotericin solution is fed to the reactor. The discs are kept under stirring during the treatment time. The pressure in the reactor is initially raised to about 100 bars using $CO_2$ (N48 $CO_2$ supplied by Air Liquid Denmark A/S) and with a temperature of about 45° C. Thereafter the temperature is raised to about 75° C. and the pressure is increased to 300 bars using further $CO_2$. After a loading time of approximately 2 hours the pressure is slowly decreased and the discs are withdrawn.

The invention claimed is:

1. A method of producing a delivery device for delivering a chemical compound, the method comprising
   i) providing an interpenetrating polymer substrate (IP substrate) comprising a first continuous polymer comprising rubber and a second polymer comprising hydrogel, where the second polymer is interpenetrating in the first polymer;
   ii) providing the chemical compound and a loading solvent for the chemical compound, the loading solvent comprising $CO_2$; and
   iii) loading the IP substrate with the chemical compound by subjecting the IP substrate to the loading solvent comprising the chemical compound under conditions where the loading solvent at least partially swells the second polymer, and
   wherein the chemical compound, the second polymer and the loading solvent are selected such that the work of adhesion ($W_{hc}$) between the second polymer and the chemical compound during at least a part of the loading is at least 10 J/m².

2. The method of claim 1, wherein the work of adhesion between the chemical compound and the second polymer during at least a part of the loading is as follows: 100 J/m² ≥ $W_{hc}$ ≥ 15 J/m².

3. The method of claim 1, wherein the rubber is a silicone rubber.

4. The method of claim 1, wherein the second polymer is a homopolymer polymerised from a monomer selected from an acrylate monomer or a vinyl polymer, styrene; oxygen-, phenyl, amino and nitrogen-containing acrylic and methacrylic derivatives; functionalized methacrylates; alkyl substituted acrylates and methacrylates; carbohydrides and fluorinated monomers, urethanes; mono- and di-functional alcohols; carboxylic acids; amines; isocyanates; epoxides; aromatics carrying alkyl group(s), sulfonated aromatics, aromatic resins, imidazol, imidazol derivatives; pyrazoles and quaternary ammonium monomers.

5. The method of claim 1, wherein the second polymer is a copolymer, polymerised from monomers comprising silanes, an acrylate monomer or a vinyl polymer, styrene; oxygen-, phenyl, amino and nitrogen-containing acrylic and methacrylic derivatives, functionalized methacrylates; alkyl substituted acrylates and methacrylates; carbohydrides and fluorinated monomers, urethanes; mono- and di-functional alcohols; carboxylic acids; amines; isocyanates; epoxides; aromatics carrying alkyl group(s), sulfonated aromatics, aromatic resins, imidazol, imidazol derivatives; pyrazoles and/or quaternary ammonium.

6. The method of claim 1, wherein the second polymer is poly(2-hydroxyethyl methacryate) (PHEMA).

7. The method of claim 1, wherein the second polymer has a max water swelling at 25° C. of about 10-10000% by mass of its dry mass.

8. The method of claim 1, wherein the second polymer has a max water swelling at 25° C. w/w of its dry mass which is higher than the max. water swelling at 25° C. w/w of the first continuous polymer.

9. The method of claim 1, wherein the IP substrate has a max water swelling at 25° C. of about 5-5000% by mass of its dry mass.

10. The method of claim 1, wherein the IP substrate comprises a continuous matrix of the first polymer and a plurality of interpenetrating paths of the second polymer.

11. The method of claim 1, wherein the IP substrate comprises a continuous matrix of the first polymer and a plurality of interpenetrating paths of the second polymer, the IP substrate has a surface and the plurality of interpenetrating paths of the second polymer coincides with said surface.

12. The method of claim 1, wherein the IP substrate is or comprises an Interpenetrating Polymer Network (IPN), the IPN being produced by providing a virgin substrate of the first continuous polymer, subjecting the virgin substrate to an extracting treatment comprising extraction of residuals, swelling the extracted virgin substrate with a solvent comprising monomers for the second polymer and polymerizing the monomers to form the IPN.

13. The method of claim 1, wherein the chemical compound, the first continuous polymer and the loading solvent are selected such that the work of adhesion ($W_{sc}$) between the first continuous polymer and the chemical compound during at least a part of at the loading is at least about 10 J/m².

14. The method of claim 1, wherein the work of adhesion for the chemical compound-first continuous polymer ($W_{sc}$) during at least a part of the loading is higher than the work of adhesion between the chemical compound and the second polymer ($W_{hc}$).

15. The method of claim 1, wherein the first continuous polymer during at least a part of the loading is swelled with the loading solvent, the relative swelling of the first continuous polymer by the loading solvent is at least about 0.2 times the relative swelling of the second polymer by the loading solvent.

16. The method of claim 1, wherein the loading solvent comprises a co-solvent which in a liquid phase can dissolve or disperse the chemical compound.

17. The method of claim 1, wherein the loading solvent comprises an organic co-solvent selected from an alcohol.

18. The method of claim 1, wherein the chemical compound is a drug, a compound for human nutrition, a compound for microbiologic nutrition, a fragrance compound, a flavor compound and/or a color compound.

19. The method of claim 1, wherein the method comprises loading the IP substrate with a plurality of chemical compounds simultaneously or in overlapping or separate steps.

20. The method of claim 1, wherein the chemical compound is not a salt.

21. The method of claim 1, wherein the chemical compound has a molar mass of up to about 90000 g/mol.

22. The method of claim 1, wherein the loading of the IP substrate with the chemical compound comprises arranging the IP substrate in a reaction chamber and at least partially swelling the second polymer with the loading solvent under conditions wherein at least a part of the loading solvent is in a sub-critical phase or supercritical phase.

23. The method of claim 1, wherein the loading of the IP substrate with the chemical compound comprises swelling the second polymer with the loading solvent comprising the chemical compound at a temperature of at least about 10° C. and an elevated pressure.

24. The method of claim 1, wherein the loading of the IP substrate with the chemical compound comprises swelling the second polymer with the loading solvent comprising the chemical compound for a period of at least about 30 minutes.

25. The method of claim 1, wherein the loading of the IP substrate with the chemical compound comprises swelling the second polymer with the loading solvent comprising the chemical compound at an elevated pressure for a preselected period, followed by lowering the pressure to about one standard atmosphere.

26. The method of claim 1, wherein the loading solvent does not dissolve the first continuous polymer or the second polymer during loading of the chemical compound.

27. The method of claim 1, wherein the loading solvent comprises a first fluid and a second fluid, wherein the first fluid during loading is in a sub-critical stage or supercritical stage and the second fluid is or comprises a co-solvent for the chemical compound, which in liquid stage can dissolve the chemical compound.

28. The method of claim 27, wherein the method comprises:
arranging the IP substrate in a reactor;
feeding the first fluid to the reactor;
feeding the second fluid with the chemical compound dissolved to the reactor; and
swelling the IP substrate with the first fluid and at least a part of the second fluid of the loading solvent to load the IP substrate with the chemical compound.

29. The method of claim 1, wherein the delivery device is
a baby nipple for adding pharmaceuticals during feeding, teething devices;
a catheter or shunt for any body fluid;
a drug delivery patch;
a nicotine patch;
a wound care product;
a surgical film;
a prophylactic device, a glove or a intravenous bag;
a contact lens;
an implant; or
a diagnostic device.

30. A method of producing a delivery device for delivering a chemical compound, the method comprising:
selecting the chemical compound and a loading solvent comprising at least 50% by mass of $CO_2$;
providing an interpenetrating polymer substrate by a method comprising providing a first continuous polymer comprising rubber and swelling the first continuous polymer with a solvent comprising monomers for a hydrogel and polymerizing the monomers to form the interpenetrating polymer substrate;
loading the interpenetrating polymer substrate with the chemical compound by subjecting the interpenetrating polymer substrate to the chemical compound dissolved in said loading solvent at a temperature of at least about 10° C. and at an elevated pressure, where the loading solvent at least partially swells the hydrogel,
wherein the monomers for the hydrogel are selected by a method comprising determining the work of adhesion ($W_{hc}$) between at least a one hydrogel and the chemical compound at a temperature of between 10 and 80° C. and identifying a hydrogel for which the determined work of adhesion ($W_{hc}$) is between 15 J/m² and 100 J/m² and selecting the monomers to be monomers for said identified hydrogel.

* * * * *